(12) United States Patent
Niazi

(10) Patent No.: US 6,638,268 B2
(45) Date of Patent: Oct. 28, 2003

(54) CATHETER TO CANNULATE THE CORONARY SINUS

(76) Inventor: Imran K. Niazi, 9080 Upper River Rd., River Hills, WI (US) 53217

( * ) Notice: Subject to any disclaimer, the term of this patent is extended or adjusted under 35 U.S.C. 154(b) by 150 days.

(21) Appl. No.: 09/828,502

(22) Filed: Apr. 6, 2001

(65) Prior Publication Data
US 2001/0052345 A1 Dec. 20, 2001

Related U.S. Application Data
(60) Provisional application No. 60/195,701, filed on Apr. 7, 2000.

(51) Int. Cl.[7] .......................................... A61M 25/098
(52) U.S. Cl. ..................... 604/528; 604/528; 604/523; 604/530; 604/164.01; 604/264; 604/96.01
(58) Field of Search ................................ 604/528, 523, 604/164.01, 530, 264, 266, 96.01, 93.01, 95.01

(56) References Cited

U.S. PATENT DOCUMENTS

| | | | | |
|---|---|---|---|---|
| 4,790,831 A | * | 12/1988 | Skrikiski | 604/282 |
| 4,886,506 A | * | 12/1989 | Lovgren et al. | 604/280 |
| 5,290,229 A | * | 3/1994 | Paskar | 604/95 |
| 5,336,182 A | * | 8/1994 | Lundquist et al. | 604/95 |
| 5,505,698 A | * | 4/1996 | Booth et al. | 604/96 |
| 5,584,803 A | * | 12/1996 | Stevens et al. | 604/4 |
| 5,643,231 A | | 7/1997 | Lurie et al. | 604/282 |
| 5,690,611 A | | 11/1997 | Swartz et al. | 604/53 |
| 5,782,741 A | | 7/1998 | Bradshaw et al. | 600/3 |
| 5,785,706 A | | 7/1998 | Bednarek | 606/41 |
| 5,807,249 A | | 9/1998 | Qin et al. | 600/374 |
| 5,824,031 A | * | 10/1998 | Cookston et al. | 607/122 |
| 5,846,229 A | * | 12/1998 | Berg | 604/281 |
| 5,879,295 A | | 3/1999 | Li et al. | 600/373 |
| 5,916,214 A | | 6/1999 | Cosio et al. | 606/41 |
| 6,001,085 A | | 12/1999 | Lurie et al. | 604/282 |
| 6,002,955 A | | 12/1999 | Willems et al. | 600/374 |
| 6,006,137 A | * | 12/1999 | Williams | 607/119 |
| 6,022,341 A | * | 2/2000 | Lentz | 604/523 |
| 6,080,151 A | | 6/2000 | Swartz et al. | 606/45 |
| 6,090,084 A | | 7/2000 | Hassett et al. | 606/281 |
| 6,093,173 A | * | 7/2000 | Balceta et al. | 604/164 |
| 6,122,552 A | * | 9/2000 | Tockman et al. | 607/116 |
| 6,179,809 B1 | * | 1/2001 | Khairkhahan et al. | 604/95.01 |
| 6,228,052 B1 | * | 5/2001 | Pohndorf | 604/96.01 |
| 6,273,881 B1 | * | 8/2001 | Kiemeneij | 604/532 |
| 2002/0103474 A1 | * | 8/2002 | Voda | 604/530 |

\* cited by examiner

*Primary Examiner*—Ira S. Lazarus
*Assistant Examiner*—Tu Cam Nguyen
(74) *Attorney, Agent, or Firm*—Philip G. Meyers (57) ABSTRACT

A double catheter includes an outer, resilient catheter having shape memory and a hook-shaped distal end, an inner, pliable catheter slidably disposed in the outer catheter and of greater length than the outer catheter so that a distal end portion of the inner catheter can be extended or retracted from a distal end opening of the outer catheter to vary the overall length of the double catheter, the inner catheter preferably having an internal lumen suitable for the introduction of contrast media, and a mechanism operable from the proximal end of the outer catheter for changing the curvature of the hook shaped distal end of the outer catheter. Such a catheter of the invention can cannulate the coronary sinus without significant manipulation.

27 Claims, 5 Drawing Sheets

CATHETER TO CANNULATE THE CORONARY SINUS

This application claims priority of U.S. Provisional Application No. 60/195,701, filed Apr. 7, 2000.

FIELD OF THE INVENTION

This invention relates to medical devices, particularly to catheters of the type used to cannulate the coronary sinus.

BACKGROUND OF THE INVENTION

The coronary sinus is a venous structure that is three to four centimeters in length and one centimeter in diameter. It forms a part of the venous drainage of the heart. The coronary sinus arises from the posterior inferior aspect of the right atrium and courses over the posterior surface of the heart, ending in the great cardiac vein. It is the final common venous drainage of most of the heart.

Cannulation of the coronary sinus has until recently not been considered important from a medical viewpoint. Medical researchers have cannulated the coronary sinus in animals and in humans to obtain information about the functioning of the heart. Cardiac surgeons will, during cardiac surgery, cannulate the coronary sinus for retrograde cardioplegia. However, routine cannulation of the coronary sinus is not performed when there is no therapeutic advantage to performing coronary sinus angiography.

It has recently become apparent that the coronary sinus and its branches can be used to place catheters (fine pacing catheters) on the epicardium of the left ventricle. The left ventricle can then be paced via these catheters. Preliminary studies show that pacing the left ventricle produces significant benefit in patients with heart failure, especially those with conduction disturbances. Therefore, studies are underway to study the coronary sinus anatomy and place the pacing catheters in the appropriate branch of the coronary sinus. Unlike for coronary arterial circulation, which has been well studied because of its therapeutic benefit, there are no presently available preformed catheters that will slip easily into the coronary sinus. U.S. Pat. No. 5,423,772 exemplifies one proposed device designed for use in the coronary sinus wherein the catheter has a double curve.

Congestive heart failure is one of the commonest diagnoses leading to hospital admission in the United States. There are 2 to 5 million patients diagnosed with CHF in the U.S. annually, and 15 million worldwide. Treatment of heart failure consists of medications, and cardiac transplantation in severe cases. Other forms of surgery, e.g. valve surgery, are also sometimes helpful. Attention has recently focused on resynchronization therapy. About 30–50% of people with severe CHF have asynchronous contraction of the cardiac chambers. This can be corrected by pacing the right atrium, the right ventricle and the left ventricle at optimal intervals to provide synchrony. Leads to pace the right atrium and right ventricle have been used for years. Recently, leads have been devised to pace the left ventricle by passing the lead through the coronary sinus into a branch vein that overlies the left ventricle. Delivery systems to guide the leads into the appropriate branch veins are now being researched.

Currently available catheters and catheter systems have several disadvantages which render lead delivery difficult. For example, the anatomy of the right atrium and the coronary sinus origin is different in patients with congestive heart failure than in patients with normal sized hearts. These differences in part form the basis for the design of the delivery system of the present invention. Such differences include that the os of the coronary sinus lies higher in the right atrium in such persons than in normal persons. The eustachian ridge is unusually prominent, and the right atrium is usually larger than normal. Subeustachian fossae are more well developed in the large right atria. There is great variation in the size of the coronary sinus and its shape and direction, and the target coronary branch veins arise at acute angles from the main coronary sinus in many patients. This renders it difficult to pass a lead into these branches. Venous valves obstruct the passage of the lead. These are variably placed, frequently close to the origin of the coronary veins. The present invention provides a catheter especially adapted for use in the coronary sinus, especially in patients suffering from congestive heart failure.

SUMMARY OF THE INVENTION

A double catheter according to one aspect of the invention includes an outer, resilient catheter having shape memory and a hook-shaped distal end configured for cannulation of the coronary sinus, an inner, pliable catheter slidably disposed in the outer catheter and of greater length than the outer catheter so that a distal end portion of the inner catheter can be extended or retracted from a distal end opening of the outer catheter to vary the overall length of the double catheter, the inner catheter preferably having an internal lumen suitable for the introduction of a fluid, such as contrast media, into the coronary sinus and also for passage of a pacing lead, and a mechanism operable from the proximal end of the outer catheter for changing the curvature of the hook shaped distal end of the outer catheter. Such a catheter of the invention can cannulate the coronary sinus without significant manipulation, enable an angiogram of the coronary sinus by means of an occlusive balloon which includes the proximal coronary sinus at the time of contrast media injection, serve as a conduit for the passage of a fine coronary sinus pacing lead (5 French in diameter), provide backup support for introducing this lead over a guide wire into the distal branches, and minimize the steps necessary for the placement of a coronary sinus lead, thereby allowing rapid introduction of such a lead.

The invention further provides a method of using a catheter to place a pacing lead in a transverse branch of the coronary sinus in order to treat a related condition such as congestive heart failure. Such a method for placing an electrical lead in a lateral branch of a coronary sinus vein using a double catheter includes the steps of inserting the catheter into the coronary sinus, advancing a guide wire through the catheter into a coronary sinus lateral branch vein, advancing the inner catheter out of a front end opening of the outer catheter along the guide wire into the branch vein, inserting the lead through the outer and inner catheters to a target location in the branch vein, and withdrawing the catheter leaving the lead in the branch vein. If necessary, the curvature of the double catheter can be adjusted in order to enter the coronary sinus. These and other aspects of the invention are discussed in the detailed description that follows.

BRIEF DESCRIPTION OF THE DRAWING

In the accompanying drawing, wherein like numeral denote like elements.

DESCRIPTION OF PREFERRED EMBODIMENTS

Figure 1:
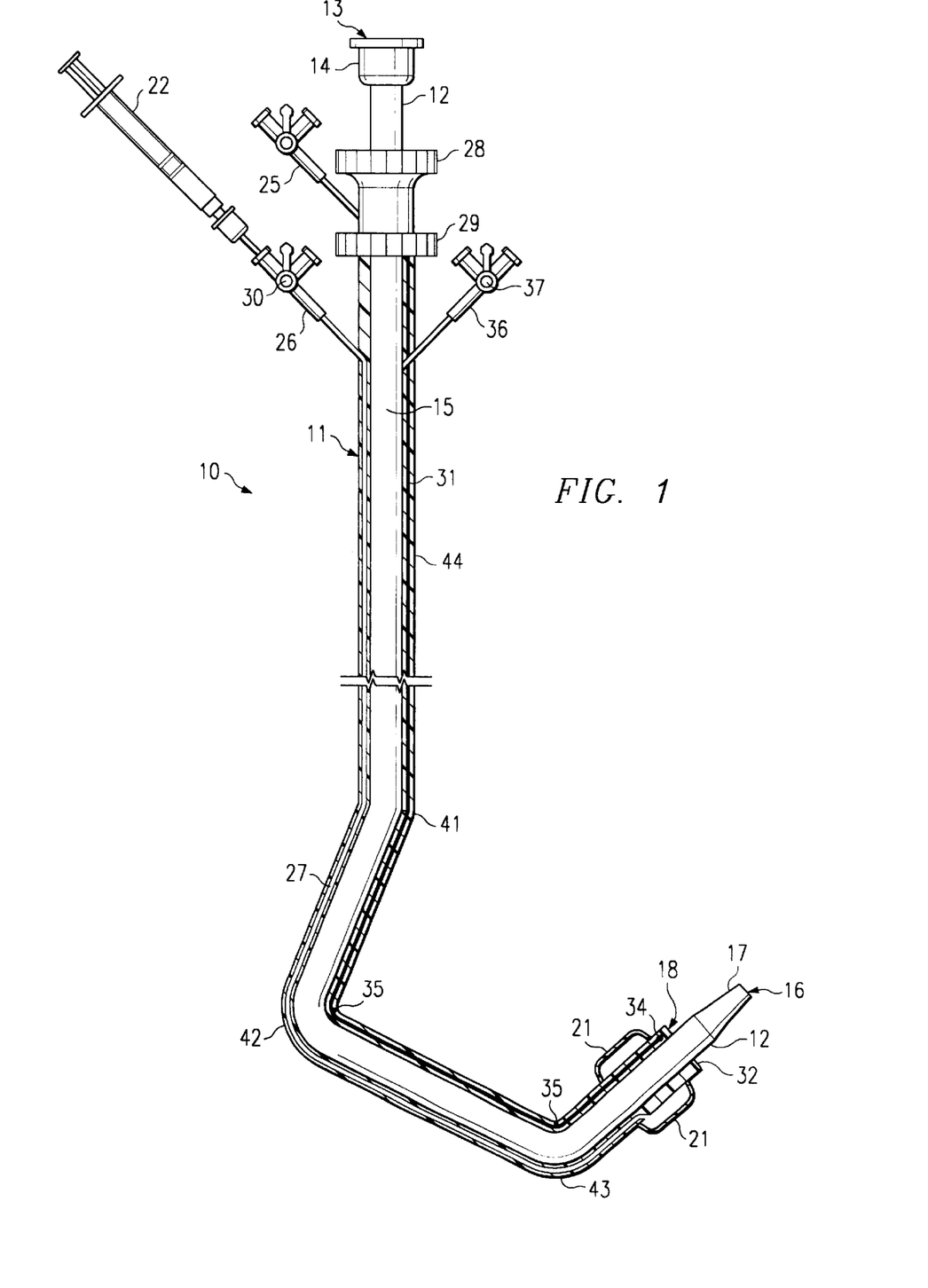
FIG. 1 is a side view of a double catheter of the invention.
Figure 2:
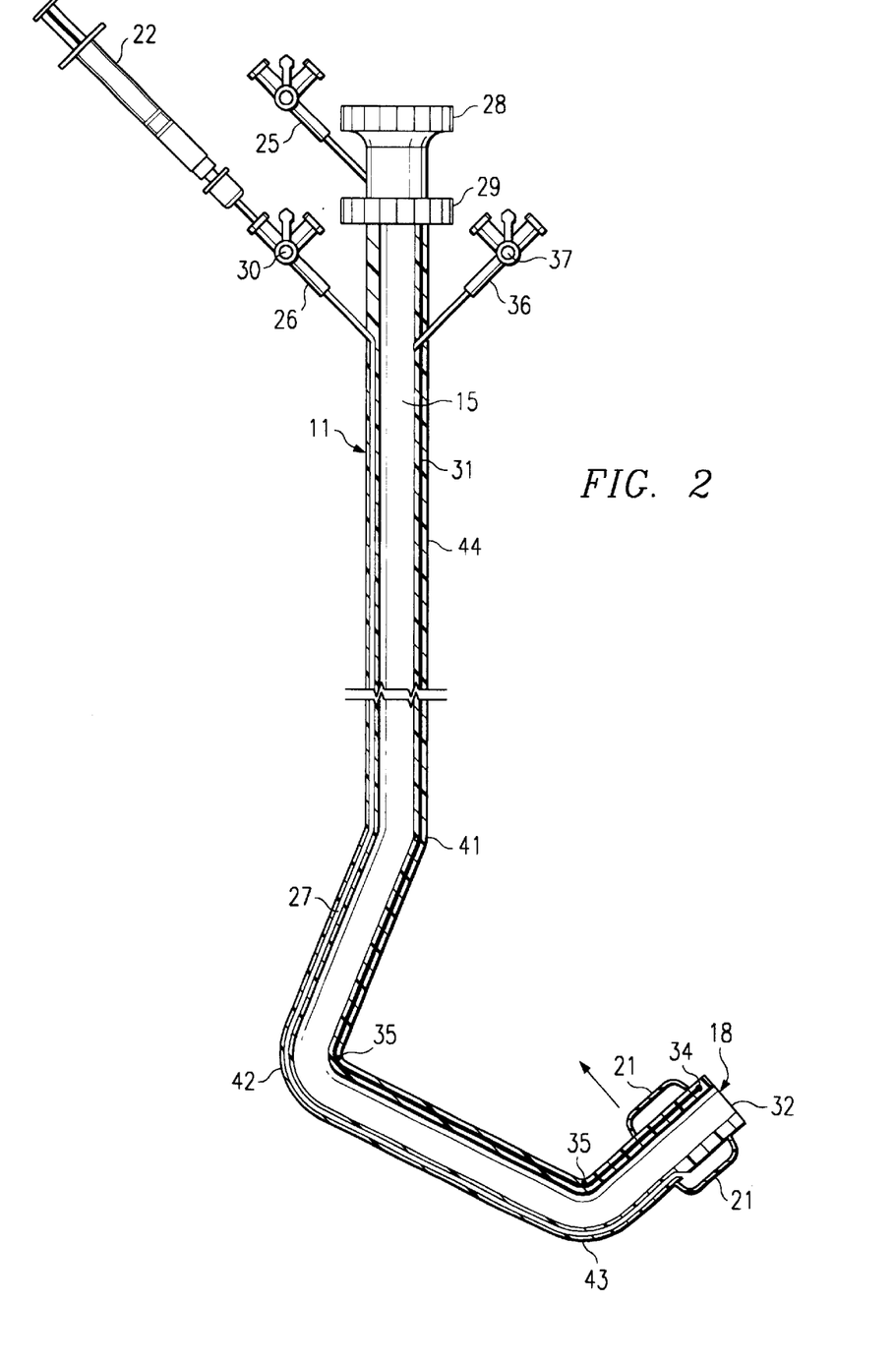
FIG. 2 is a side view of the outer catheter of FIG. 1.

FIGS. 1 and 2 illustrate a double catheter 10 according to the invention having a typical length of 60 cm. An outer catheter 11 is made of a braided silastic or similar material to allow torque control and stiffness. An inner catheter 12, which slides in and out of outer catheter 11, is constructed of a more pliable, soft material such as silicone. The combination of outer and inner catheters 11, 12 provides a number of advantages, including variability in the reach of the catheter, and outer catheter stiffness necessary for manipulation along with inner catheter softness, which permits safe cannulation of the coronary sinus and advancement of catheter 11 into the distal coronary sinus for purposes of support. It also allows the inner catheter 12 to conform to the torturous course of a coronary sinus.

Inner catheter 12 fits into lumen 15 of outer catheter 11, and is preferably coated with a hydrophilic lubricious material which allows catheter 12 to slide in and out of outer catheter 11 with ease. A proximal end 13 of inner catheter 12 terminates in a hemostatic valve 14 having an adjustable diaphragm. Valve 14 prevents leakage of blood when a 5 French pacing lead is introduced through inner catheter 12 into the coronary system. Preferably, a distal end 16 of inner catheter 12 has a tip 17, for example, about 1 cm long, made of a material softer than the remainder of inner catheter 12. This may, for example, be accomplished by making tip 17 thinner than the remainder of catheter 12, or by making a bilayered inner catheter 12 wherein the one layer extends further than the other to form the tip and optionally is made of a material softer than that of the other layer.

Outer catheter 11 has several functions. Because of its stiffness and torque, it can be manipulated in the right atrium to allow cannulation of the coronary sinus. Such stiffness also lends support to the pacing lead as it is introduced into the distal coronary sinus. A distal end 18 of outer catheter 11 has an external inflatable cuff or balloon 21. Balloon 21 can be inflated with air by means of a syringe 22 connected to balloon 21 as described below. Inflation of balloon 21 allows occlusion of the proximal coronary sinus, which is necessary for obtaining a coronary sinus angiogram.

The proximal end of outer catheter 11 has several features. A port 26 including a shutoff valve 30 is provided for introduction of air into balloon 21. This port 26 is connected by means of a passage 27 in the wall of catheter 11 with the distal balloon 21. A torque coupling 28 of a type known in the art may be tightened down on inner catheter 12 to prevent it from moving within outer catheter 11. A torque screw 29 is attached to a cable or wire 31 that runs in the wall of outer catheter 11 and may be wound over one or more small rounded corners or small pulleys 35 set in the wall of catheter 11. This cable 31 is anchored, as by embedding a enlarged end thereof, at a point 34 close to a tip 32 of outer catheter 11. Rotation of torque screw 29 causes cable 31 to be retracted, which changes the shape of the outer catheter 11 (making the hooked shape more pronounced as shown by the arrow) and counter-rotation does the opposite. Torque screw 29 may, for example, comprise a spool or reel having an external circumferential groove on which cable 31 is attached and is wound or unwound as needed. A port 36 with an associated shutoff valve 37 is provided through the wall of outer catheter 11 for delivering a saline flush through lumen 15.

For optimum deployment in the coronary sinus, inner and outer catheters 11, 12 preferably have a predetermined shape and a certain degree of stiffness to maintain such shape during manipulation in the heart, but still flexible enough to bend when required. As shown in FIG. 2, the hook-shaped distal end of outer catheter 11 may comprise substantially straight segments spanning three bends 41, 42 and 43. First bend 41 adjoining a straight, proximal portion 44 of outer catheter 11 is in the range of about 130° to 180°, especially 130° to 175°. Second, intermediate bend 42 extends in a direction opposite bend 41 and is in the range of about 75° to 100°. Third bend 43 near the distal end of outer catheter 11 extends in the same direction as bend 42 and is in the range of about 130° to 175°. These ranges refer to the angle formed by the straight segments adjacent each bend when the catheter is in an undistorted state. Operation of the deflection device to tighten the cable will reduce these angles, especially for second bend 42. The material of which outer catheter 11 is made, e.g. silastic, has sufficient shape memory to return to its original shape when undistorted. The undistorted shape of outer catheter 11 can be varied and catheter 10 thereby made in several sizes to accommodate different heart sizes. For example, for a normal size atria with a prominent Eustachian valve, outer catheter 11 may be substantially J-shaped with no first bend (bend 41=180°), whereas for large atria with a prominent Eustachian valve, it may be useful to make catheter 11 more in a question mark shape (shown inverted in FIGS. 1–2).

Coronary sinus catheter 10 may be deployed in the following fashion. Distal balloon 21 is deflated, inner catheter 12 is withdrawn completely into outer catheter 11, and catheter 10 is inserted through a venous sheath introduced in the left XX subclavian vein. It is guided into the right atrium over a guide wire, and the guide wire and sheath are then removed. Catheter 10 is rotated until tip 17 lies within the tricuspid valve, then advanced until tip 17 is seen to lie in the inferior-most portion of the tricuspid valve. If the reach of catheter 10 in this configuration is not sufficient to cannulate the tricuspid valve, then inner catheter 12 is advanced out of outer catheter 11 to make the entire system longer.

Subsequent manipulation is carried out in a left anterior fluoroscopic view. Counterclockwise torque is exerted on catheter 10. At the same time, inner catheter 12 is gradually withdrawn. Eventually, catheter 10 slips over the tricuspid annulus and, because of the counterclockwise torque, twists and pops into the proximal coronary sinus. In some instances, it may come to lie at the mouth of the proximal coronary sinus. In that case, inner catheter 12 is gradually advanced until the coronary sinus is cannulated. Once the coronary sinus is cannulated, inner catheter 12 is advanced as far as it will go into the coronary sinus and/or great cardiac vein. Distal balloon 21 on outer catheter 11 is inflated using syringe 22 to occlude the proximal coronary sinus. Contrast medium is injected via a port 25 through the lumen of inner catheter 12 to obtain a coronary sinus angiogram. Port 36 is then hooked up to a saline flush. A coronary sinus lead is introduced through a hemostasis valve 14 into inner catheter 12. It is positioned using a guide wire in an appropriate branch of the coronary sinus.

Figure 3:
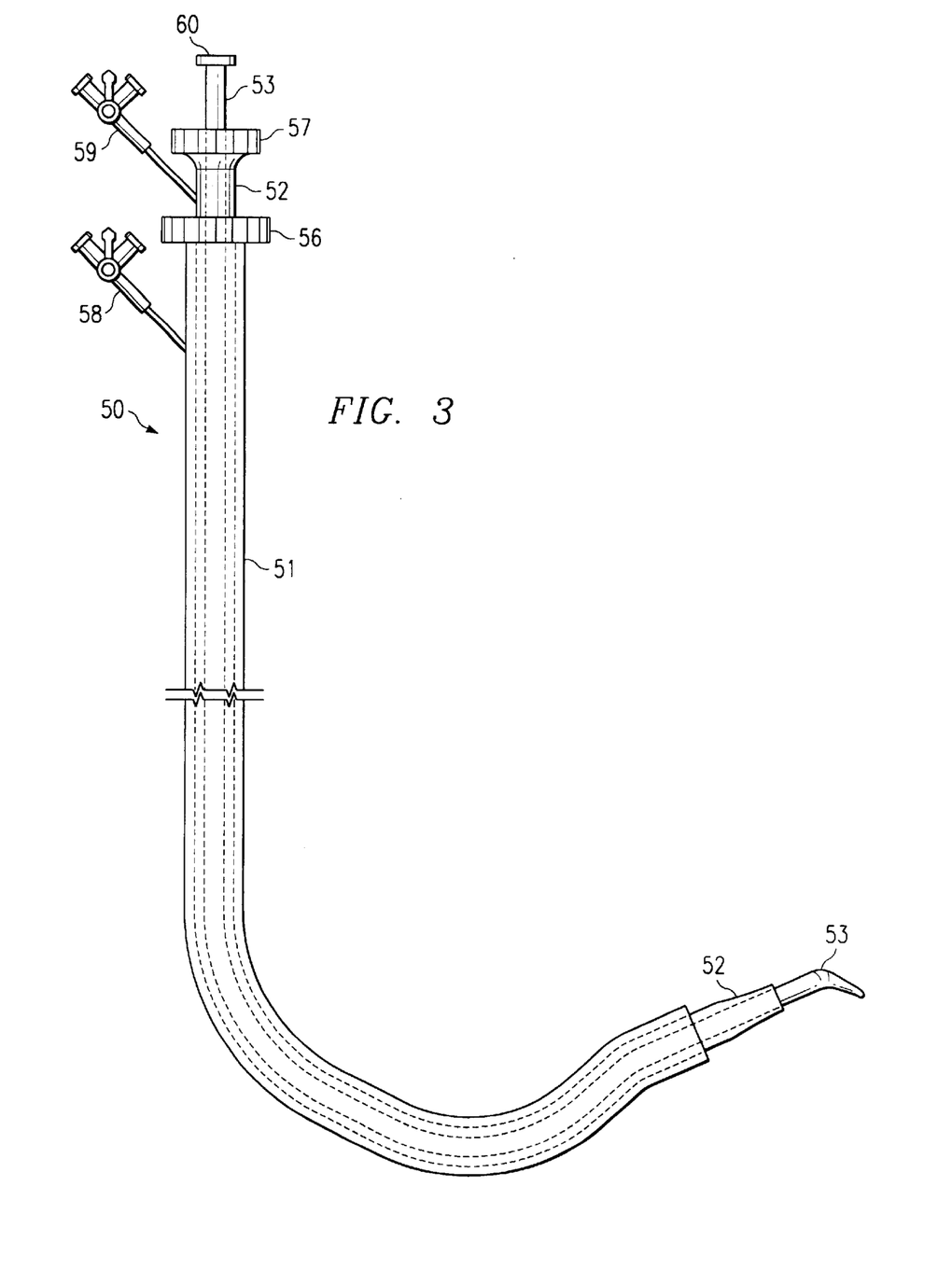
FIG. 3 is a side view a second embodiment of a catheter according to the invention.

A triple catheter 50 according to the invention is designed to overcome the obstacles described above that are encountered with congestive heart failure patients and further provide a more economical catheter system that does not rely on specialized miniature adjustment mechanisms. The system includes an outer guide catheter 51, an inner guide catheter 52 nested therein, an obturator 53 nested inside the inner guide 52. In one example, outer guiding catheter 51 is 2.9 mm in outer diameter, 2.6 mm inner diameter. It is relatively stiff and has a braided design, which lends support and one-for-one torque control. In this respect, it can resemble an angioplasty guiding catheter. The shape of outer guiding catheter 51 is similar, but not identical, to a left amplatz curve. The proximal end terminates in an screw-adjusted hemostatic valve 56, to allow introduction of leads or wires of different diameters without leakage of blood. There is also a side-port 58, preferably with a 3-way valve, to allow injection of contrast medium and saline.

Inner guiding catheter 52 made of a soft, pliable material such as silicone, and in this example is 2.6 mm in outer diameter and 2.3 mm in inner diameter. It has no longitudinal braiding, which makes it extremely flexible and able to conform to various shapes. Inner catheter 52 is designed to advance over a guide wire into a side branch of the coronary sinus, in conjunction with the obturator 53. Its flexibility allows it to negotiate tortuous vessels and side branches that originate from the coronary sinus at an acute angle, yet it still possesses the radial strength needed to prevent it from collapsing when obturator 53 is withdrawn. Inner guide 52 is longer than outer guide 51, e.g., 68 cm in length. The proximal end of guide 52 has a hemostasis valve 57 to prevent back bleeding and a side port 59 to permit contrast medium injection.

Obturator 53 is preferably made of very pliable silicone, and has a central lumen that will accommodate an 0.038 inch guide wire. Obturator 53 fits into inner guide 52, and in one embodiment is 70 mm long, 2.1 mm in outer diameter tapering to 1.25 mm diameter at its tip. In use, obturator 53 tracks over a 0.038" guide wire 81 into a targeted side branch 56, in concert with the inner guide catheter 52. A tapered tip 71 of obturator 53 may protrude from the front end opening of inner catheter 52. Without such a protruding tip 71, the edge of inner catheter 52 might catch on venous valves or sharp angles. The terminal 7 mm of obturator 53 may have a bend 72 therein of up to about 30 degrees, i.e., defining an angle from 150–180 degrees. This allows tip 71 to function as a guiding device for the 0.038" guide wire 81, which can then be directed into acutely angled side branches. The proximal end of obturator 53 terminates in a standard port 60 allowing attachment of a 10 cc syringe.

Figure 7:
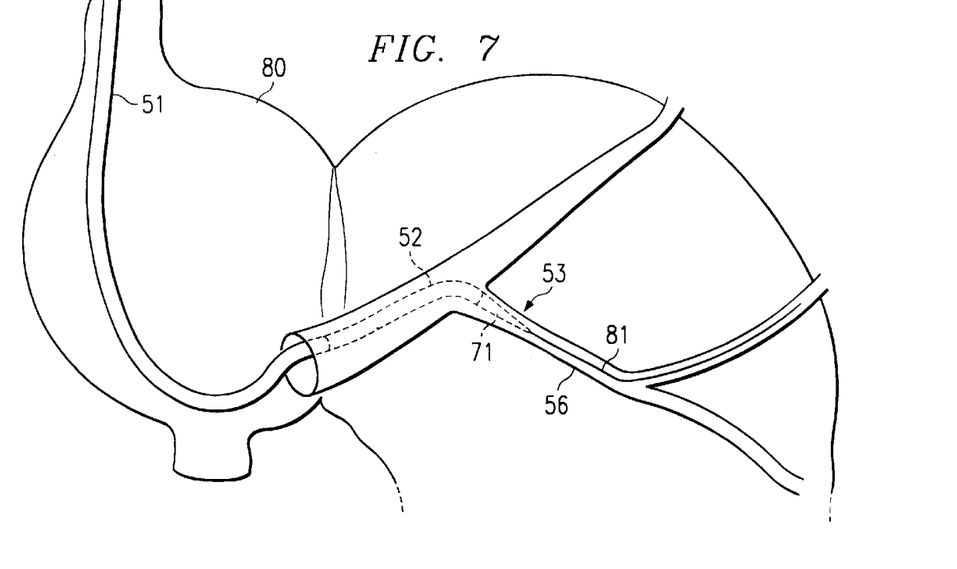
FIGS. 7 and 8 are diagrams illustrating use of the catheter of FIG. 3 a method of introducing a pacing lead according to the invention.
Figure 8:
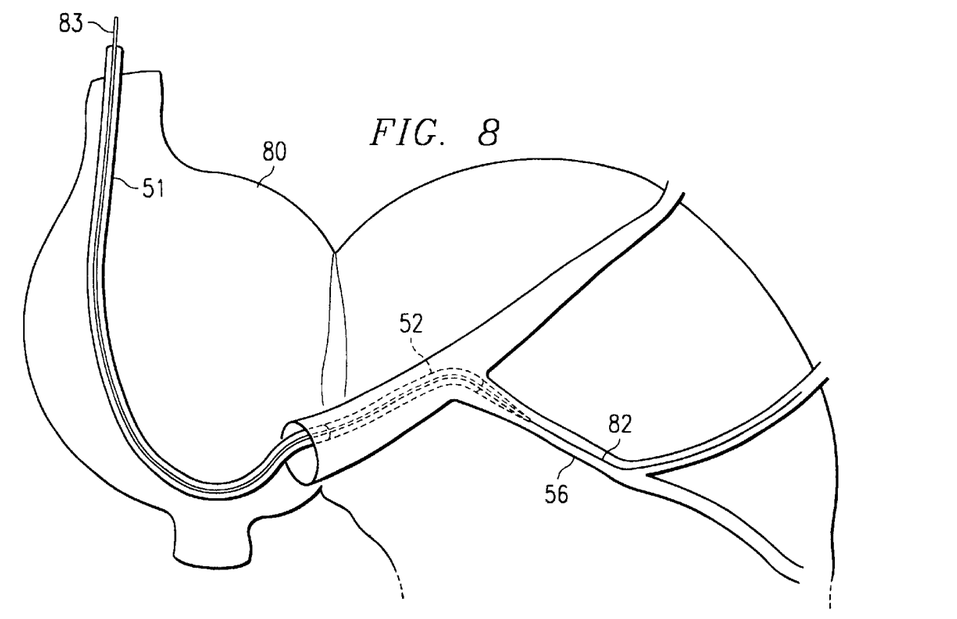

Referring to FIGS. 7 and 8, outer guiding catheter 51 is initially connected to a syringe and pressure monitoring system and then inserted into the right atrium 80. The physician attempts to use it to cannulate the coronary sinus without the use of the other components. If this succeeds, an 0.038" hydrophillic-coated guide wire 81 is advanced through it, and used to cannulate the target lateral coronary sinus side-branch 56. (If the side branch 56 cannot be easily cannulated, the angled obturator 53 can be extended and used to direct the guide wire 81 as illustrated in FIG. 7.) The inner guide 52, with obturator 53 inside, is then passed through outer guide 52 over the 0.038" wire into the target side branch 56. Obturator 53 is then withdrawn, and an electrical lead 83 is then advanced through the catheter over a 0.014" guide wire 82 to its final resting place in the target branch 56, and ultimately connected to a pacemaker after the catheter is withdrawn in order to apply electrical heart stimulation to that location. Guide wire 82 is only used if needed; it may be possible to place lead 83 without it.

An advantage of this three-part system is that it allows a standard lead (not an over-the-wire design) to be positioned in a transverse branch 56 which has a relatively sharp angulation at its origin from the main coronary sinus. Although not deflectable using an screw adjustment mechanism as described above in connection with the first embodiment, this embodiment can nevertheless be used to cannulate the coronary sinus whether the latter is placed normally, higher than normal, or lower than normal. The angle of outer guide 51 can be changed by inserting or withdrawing the inner guide 52. Inserting inner guide 52 without obturator 53 before cannulation straightens outer guide 51, i.e., makes the angle of the outer guide 51 shallower, allowing engagement of a lower origin of the coronary sinus. Inserting both obturator 53 and inner guide 52 makes the outer guide angle even shallower. Thus, the outer guide alone, the outer guide plus inner guide, and outer guide plus inner guide plus obturator can be used as needed to cannulate coronary sinuses of varying heights of origin.

Figure 4:
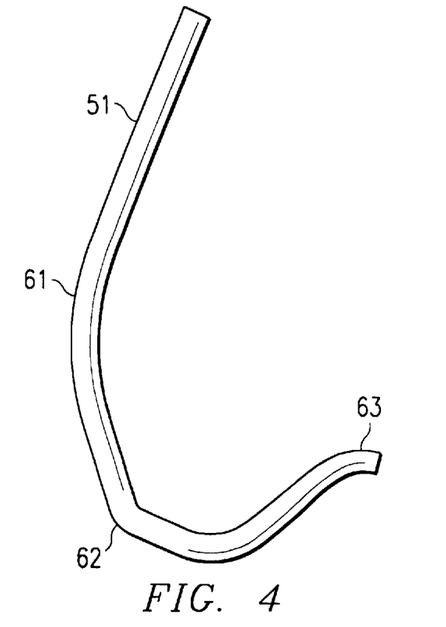
FIGS. 4 and 5 are diagrams illustrating preferred shapes for the outer guide and obturator of FIG. 3.

This three-part telescoping embodiment thus eliminates the need for a cable system to change the curvature of the catheter during manipulation As shown in FIG. 4, outer guide catheter 51 preferably has three bends in a manner similar to outer catheter 11, with the first or proximal bend 61 ranging from about 150–180 degrees, the second (middle) bend 62 ranging from about 120–180 degrees, and the third proximal bend from 90 to 160 degrees in a direction opposite to that of the other two bends, as shown. Inner guide catheter 51 preferably has three bends in a manner similar to the outer catheter 11, with the first or proximal bend 61 ranging from about 150–180 degrees, the second (middle) bend 62 ranging from about 120–180 degrees, and the third proximal bend 63 from 90 to 160 degrees in a direction opposite to that of the other two bends, as shown. In one preferred form, outer guide 51 is 9 French diameter, 60 cm length, inner guide 52 is made of a soft material 8 French diameter, 68 cm length, and obturator 53 is 5 French diameter, 75 cm length.

Figure 5:
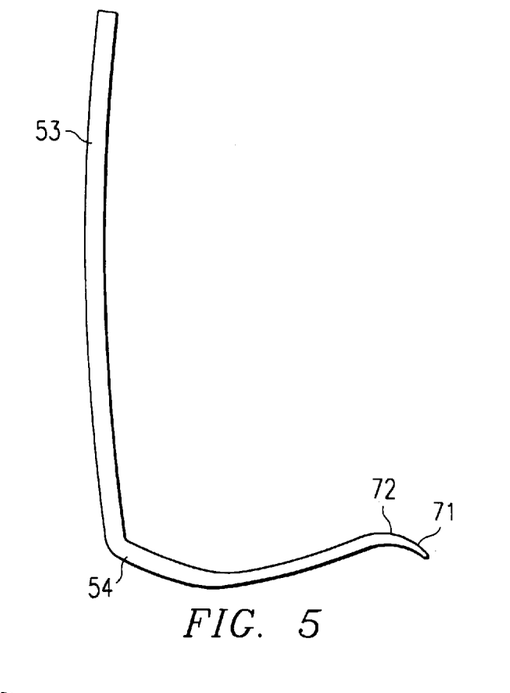

Referring to FIG. 5, obturator 53 stiffens and shapes inner guide 52 when inside of it. It may be pre-formed with a right angle bend 54 as shown to conform more easily to the shape of outer guide 51, but this is not essential. However, tip 71 of obturator is 53 bent to an angle in the range of about 150–180 degrees to better aid in introducing a lead into a transverse vein as described above. Obturator 53 preferably tapers to a blunt point having a small opening therein just large enough to admit the largest size guide wire to be used in the procedure, in this example, 0.038 inch.

Figure 6:
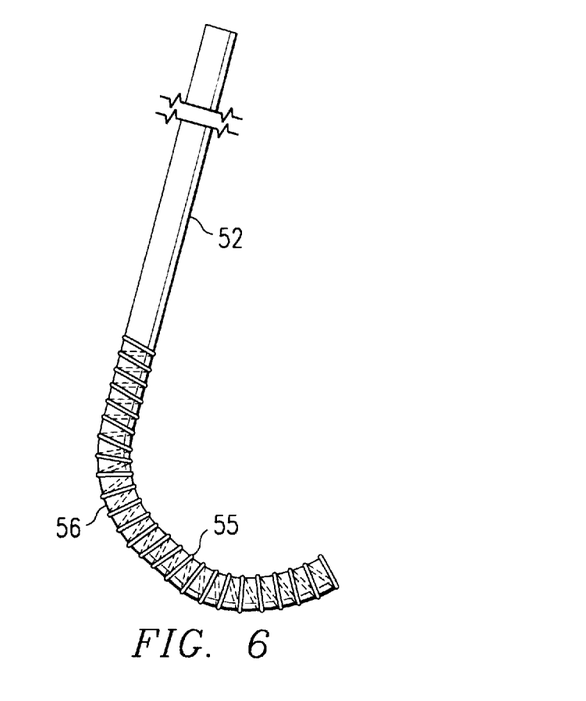
FIG. 6 is a diagram illustrating an alternative inner catheter for use in the embodiment of FIG. 3.

In an alternative version of catheter 50, the radial strength of the inner guide or catheter 52 prevents its collapse when obturator 53 is withdrawn. For this purpose, as shown in FIG. 6, a bend 56 in inner guide 52 is reinforced with a helical wire coil 55 that is embedded therein, or a series of spaced wire rings or hoops. These hoop reinforcements prevent inner guide 52 from collapsing during withdrawal of obturator 53 but do not prevent inner guide 52 from bending in a flexible manner.

The claims which follow define certain aspects of the invention but do not limit the invention. It will be evident, for example, that a catheter according to the invention can be used to reach other hard to access parts of the human body, both in the heart and elsewhere, due to its unique structure.

What is claimed is:

1. A double catheter, comprising:
    an outer, resilient catheter having shape memory and a hook shaped distal end configured for cannulation of the coronary sinus with at least one curved bend;
    an inner, pliable catheter slidably disposed in the outer catheter and of greater length than the outer catheter so that a distal end portion of the inner catheter can be extended or retracted from a distal end opening of the outer catheter to vary the overall length of the double catheter, the inner catheter having an internal lumen configured for the introduction of contrast media and a pacing lead into the coronary sinus; and a mechanism operable from the proximal end of the outer catheter for changing the curvature of the distal end of the outer catheter.

2. The double catheter of claim 1, wherein the mechanism for changing the curvature of the hook shaped distal end further comprises an obturator slidably disposed inside of the inner catheter, wherein the obturator is configured to reduce the curvature of the hook shaped distal end when inserted in the inner catheter.

3. The double catheter of claim 1, further comprising a balloon mounted on the outside of the distal end of the outer catheter positioned for occlusion of the proximal coronary sinus, and a conduit permitting inflation of the balloon at the proximal end of the outer catheter.

4. A double catheter, comprising:
an outer, resilient catheter having shape memory and a hook-shaped distal end with at least one curved bend;
an inner, pliable catheter slidably disposed in the outer catheter and of greater length than the outer catheter so that a distal end portion of the inner catheter can be extended or retracted from a distal end opening of the outer catheter to vary the overall length of the double catheter, the inner catheter having an internal lumen suitable for the introduction of a fluid therethrough; and
a mechanism operable from the proximal end of the outer catheter for changing the curvature of the distal end of the outer catheter, wherein the mechanism for changing the curvature of the hook shaped distal end comprises a cable anchored to the outer catheter at a point proximate the distal end of the outer catheter and at a point proximate the proximal end of the outer catheter, whereby shortening of the cable from the point proximate the proximal end of the outer catheter results in increased curvature of the hook shaped distal end.

5. The double catheter of claim 4, wherein the cable runs inside a wall of the outer catheter.

6. The double catheter of claim 1, further comprising a mechanism operable from a proximal end of the outer catheter for securing the inner catheter against sliding movement relative to the outer catheter.

7. The double catheter of claim 6, further comprising a port for introducing a fluid into a space between the inner and outer catheters.

8. The double catheter of claim 1, wherein the hook-shaped distal end comprises substantially straight segments spanning three bends.

9. The double catheter of claim 8, wherein a first bend adjoining a straight, proximal portion of the outer catheter is in the range of 130° to 175°, a second, intermediate bend is in the range of 75° to 100°, and a third bend nearest the distal end of the outer catheter is in the range of to 130° to 175°.

10. The double catheter of claim 1, wherein the mechanism for changing the curvature of the hook shaped distal end comprises a portion of the inner catheter configured to reduce the curvature of the hook shaped distal end when inserted in the outer catheter.

11. A method for placing an electrical lead in a lateral branch of a coronary sinus vein using a double catheter including an outer catheter and an inner catheter slidably disposed inside the outer catheter, comprising:
inserting the catheter into the coronary sinus;
advancing a guide wire through the catheter into a coronary sinus lateral branch vein;
advancing the inner catheter out of a front end opening of the outer catheter along the guide wire into the branch vein;
inserting the lead through the outer and inner catheters to a target location in the branch vein; and
withdrawing the catheter leaving the lead in the branch vein.

12. The method of claim 11, further comprising:
adjusting the curvature of the double catheter in order to enter the coronary sinus.

13. An outer catheter configured for use with an inner, pliable catheter which can be slidably disposed in the outer catheter and of greater length than the outer catheter so that a distal end portion of the inner catheter can be extended or retracted from a distal end opening of the outer catheter, the outer catheter comprising a resilient tube having shape memory and sufficient stiffness to permit advancement of the outer catheter into a distal coronary sinus, and having a hook-shaped distal end wherein a first bend adjoining a straight, proximal portion of the outer catheter is in the range of 130° to 180°, a second, intermediate bend is in the range of 75° to 100° in a direction opposite the first bend, and a third bend nearest the distal end of the outer catheter in the same direction as the second bend is in the range of to 130° to 175°.

14. The catheter of claim 13, wherein the first bend equals 180°, rendering the outer catheter substantially J-shaped.

15. The catheter of claim 13, wherein the first bend is in the range of 130–175°, rendering the outer catheter substantially question mark-shaped.

16. The catheter of claim 13, wherein the outer catheter is made of a braided silastic.

17. The catheter of claim 13, wherein the outer catheter further comprises:
an external inflatable cuff near the distal end of the outer catheter; and
means for inflation of the cuff sufficient to permit occlusion of the proximal coronary sinus.

18. A double catheter, comprising:
an outer catheter comprising a resilient tube having shape memory and sufficient stiffness to permit advancement of the outer catheter into a distal coronary sinus, and having a hook-shaped distal end wherein a first bend adjoining a straight, proximal portion of the outer catheter is in the range of 130° to 180°, a second, intermediate bend is in the range of 75° to 100° in a direction opposite the first bend, and a third bend nearest the distal end of the outer catheter in the same direction as the second bend is in the range of to 130° to 175°, and
an inner, pliable catheter slidably disposed in the outer catheter and of greater length than the outer catheter so that a distal end portion of the inner catheter can be extended or retracted from a distal end opening of the outer catheter to vary the overall length of the double catheter, wherein the inner catheter has an internal lumen suitable for the introduction of a fluid therethrough and a hemostatic valve at a proximal end thereof that prevents leakage of blood when a pacing lead is introduced through the inner catheter into the coronary system.

19. The double catheter of claim 18, wherein the first bend equals 180°, rendering the outer catheter substantially J-shaped.

20. The double catheter of claim 18, wherein the first bend is in the range of 130–175°, rendering the outer catheter substantially question mark-shaped.

21. The double catheter of claim 18, wherein the outer catheter is made of a braided silastic.

22. The double catheter of claim 18, wherein the outer catheter further comprises:

an external inflatable cuff near the distal end of the outer catheter; and means for inflation of the cuff sufficient to permit occlusion of the proximal coronary sinus.

23. The double catheter of claim 18, further comprising a mechanism operable from a proximal end of the outer catheter for changing the curvature of the distal end of the outer catheter.

24. A method for placing a electrical lead in a lateral branch of a coronary sinus vein using a double catheter including an outer catheter comprising a resilient tube having shape memory and sufficient stiffness to permit advancement of the outer catheter into a distal coronary sinus, and having a hook-shaped distal end, and an inner, pliable catheter slidably disposed in the outer catheter and of greater length than the outer catheter so that a distal end portion of the inner catheter can be extended or retracted from a distal end opening of the outer catheter to vary the overall length of the double catheter, the method comprising:

inserting the catheter into the coronary sinus;

advancing a guide wire through the catheter into a coronary sinus lateral branch vein;

advancing the inner catheter out of a front end opening of the outer catheter along the guide wire into the branch vein;

inserting the lead through the outer and inner catheters to a target location in the branch vein; and withdrawing the catheter leaving the lead in the branch vein.

25. The method of claim 24, wherein a first bend adjoining a straight, proximal portion of the outer catheter is in the range of 130° to 180°, a second, intermediate bend is in the range of 75° to 100° in a direction opposite the first bend, and a third bend nearest the distal end of the outer catheter in the same direction as the second bend is in the range of to 130° to 175°.

26. The method of claim 25, wherein the first bend equals 180°, rendering the outer catheter substantially J-shaped.

27. The method of claim 25, wherein the first bend is in the range of 130–175°, rendering the outer catheter substantially question mark-shaped.

* * * * *